(12) United States Patent
Tribut et al.

(10) Patent No.: US 8,890,550 B2
(45) Date of Patent: Nov. 18, 2014

(54) ELECTRICAL DEVICE FOR DETECTING MOISTURE

(75) Inventors: Laurent Tribut, Saint Jean de Soudain (FR); Yann Breton, Villeurbanne (FR); Ivar Granheim, Oslo (NO)

(73) Assignee: Nexans, Paris (FR)

(*) Notice: Subject to any disclaimer, the term of this patent is extended or adjusted under 35 U.S.C. 154(b) by 254 days.

(21) Appl. No.: 13/275,577

(22) Filed: Oct. 18, 2011

(65) Prior Publication Data
US 2012/0126838 A1   May 24, 2012

(30) Foreign Application Priority Data
Oct. 21, 2010  (FR) ...................... 10 58586

(51) Int. Cl.
| | | |
|---|---|---|
| *G01R 27/08* | (2006.01) | |
| *G01N 27/04* | (2006.01) | |
| *G01M 3/16* | (2006.01) | |
| *G01N 27/12* | (2006.01) | |

(52) U.S. Cl.
CPC ............ *G01N 27/121* (2013.01); *G01N 27/048* (2013.01); *G01M 3/165* (2013.01)
USPC ................ 324/694; 324/643; 73/73; 340/602

(58) Field of Classification Search
USPC ......................... 324/643, 694; 73/73; 340/602
See application file for complete search history.

(56) References Cited

U.S. PATENT DOCUMENTS

| | | | |
|---|---|---|---|
| 6,144,209 A * | 11/2000 | Raymond et al. | 324/512 |
| 7,212,009 B2 * | 5/2007 | Raymond et al. | 324/539 |
| 8,256,269 B2 * | 9/2012 | Raymond | 73/40 |
| 8,601,679 B2 * | 12/2013 | Raymond | 29/828 |
| 8,664,963 B2 * | 3/2014 | Reese et al. | 324/693 |
| 2004/0030032 A1 * | 2/2004 | Manabe et al. | 524/502 |

FOREIGN PATENT DOCUMENTS

| | | | | |
|---|---|---|---|---|
| WO | 2010046886 | | 4/2010 | |
| WO | WO 2010046886 A2 * | | 4/2010 | G01M 3/04 |

* cited by examiner

*Primary Examiner* — Patrick Assouad
*Assistant Examiner* — Sean Curtis
(74) *Attorney, Agent, or Firm* — Sofer & Haroun, LLP

(57) ABSTRACT

An electrical device for detecting moisture has a detection cable (10*a*, 10*b*, 10*c*) made up of a first element (1) and of a second element (2*a*, 2*b*, 2*c*) which elements are elongate and electrically conducting and separated by a polymer-based material (3), and an electrical resistance measurement appliance intended to measure the electrical resistance between the first and second elements of the the cable, where the material (3) is a non-soluble and moisture-sensitive material.

12 Claims, 3 Drawing Sheets

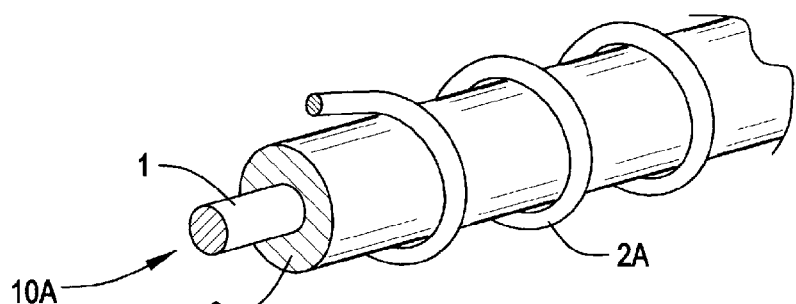
FIG. 1
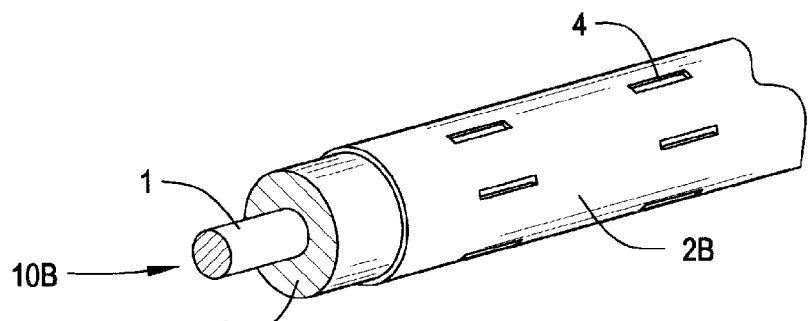
FIG. 2
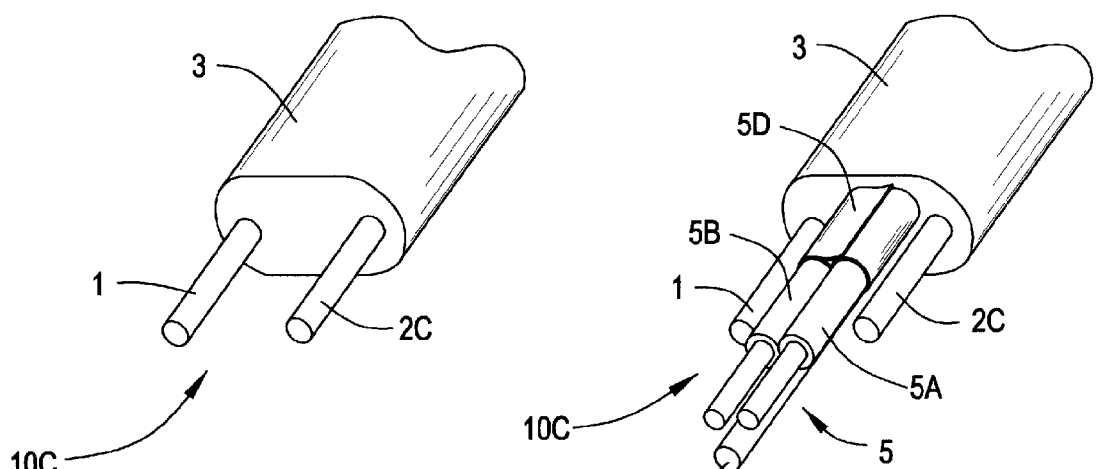
FIG. 3
FIG. 4

ELECTRICAL DEVICE FOR DETECTING MOISTURE

RELATED APPLICATION

This application claims the benefit of priority from French Patent Application No. 10 58586, filed on Oct. 21, 2010, the entirety of which is incorporated by reference.

BACKGROUND

1. Field of the Invention

The present invention relates to an electrical device for detecting moisture, comprising a detection cable.

It applies typically, although not exclusively, to a large-sized electrical device that can, for example, be placed into a partition, along a wall, or under a roof covering.

2. Description of Related Art

The issue is that slow ingress of moisture into the walls or roof covering of a house can lead to the spread of mold and other microorganisms making the home unsanitary. Detecting the level of moisture in this type of element using a pointwise moisture sensor is inappropriate in this specific instance and it is therefore necessary to use devices that detect moisture over a long distance, such as a detection cable.

By way of example, mention may be made of document WO2010/046886 which describes an electrical device for detecting moisture and which comprises a detection cable. The said detection cable is made up of a first electrical wire and of a second electrical wire which wires are separated by a polymer material.

These two electrically conducting elements (i.e. electrical wires) are connected at one end of the cable to an ohmmeter, thus allowing the electrical resistance of the cable to be measured periodically or continuously.

The polymer material used is a water soluble polymer material. Thus, when said material is dry and intact, no current is detected between the two electrical wires because these two wires are separated by the polymer material which is electrically insulating. It the polymer material comes into contact with water, it dissolves and allows the two electrical wires to come into contact with one another. Thus the resistance between the two wires drops significantly and for example identifies an ingress of water.

OBJECTS AND SUMMARY

However, because of the solubility of the polymer material, this electrical device of the prior art cannot be used more than once if moisture has already come into contact with said material. Thus, the cost of such a device ultimately proves to be relatively high in relation to its use.

The object of the present invention is to alleviate the disadvantages of the techniques of the prior art by notably offering an economical electrical device for detecting moisture, comprising a detection cable, that can be used several times while at the same time guaranteeing electrical resistance measurements that are reliable and repeatable.

The subject of the present invention is an electrical device for detecting moisture, comprising:
- a detection cable made up of a first element and of a second element which elements are elongate and electrically conducting, preferably separated and separated only, by a polymer-based material, and
- an electrical resistance measurement appliance intended to measure the electrical resistance between the first and second elements of the said cable, the device being characterized in that the polymer-based material (i.e. polymer material) is a non-soluble and moisture-sensitive material.

What is meant by "moisture" is water in the form of liquid and/or vapor.

What is meant by a "non-soluble material" is a material that can substantially not be dissolved or put into solution in a solvent, the solvent preferably being water. In other words, the material loses substantially no mass when immersed, notably over a period of 24 h, in a solvent, the solvent preferably being water. Thus, the polymer material of the invention does not undergo irreversible degradation when brought into contact with said solvent.

What is meant by a "moisture-sensitive material" is a material that has physico-chemical properties that are necessary and sufficient for moisture to be adsorbed onto its surface and diffused through said material.

For preference, the distance separating the two elongate elements is substantially constant along the length of the detection cable or, in other words, the thickness of the polymer material is substantially identical along the length of the detection cable, so as to obtain electrical resistance measurements that are reliable and representative of the environment in which the detection cable is located.

The device according to the invention makes it possible to detect the ingress of moisture and thus avoid the spread of microorganisms that evolve in damp environments. One significant advantage is that it can be re-used once the moisture has evaporated from the detection cable while at the same time guaranteeing detection that is reliable and repeatable even after several detections of moisture, because the polymer material of which the cable is mode is not soluble, particularly in water.

Of course, the apparatus for measuring the electrical resistance is connected to the two electrically conducting elements at one of the ends of the detection cable. The two electrically conducting elements at the other end of the detection cable are themselves electrically insulated, for example using a heat-shrink polymer sleeve.

Thus, as the moisture content increases, electrical resistance measured by the electrical resistance measurement appliance between the two electrically conducting elements decreases: an ohmic drop is therefore observed. Specifically, what happens is that the moisture adsorbed and diffused through the polymer material of the invention creates conductive "bridges" and thus forms a "closed" electrical circuit between the two electrically conducting elements which are therefore no longer "insulated" by the polymer material that separates them: the polymer material becomes "electrically conducting".

For preference, the ohmic drop is of the order of at least one decade, preferably of at least two decades, and as a special preference of at least three decades.

According to a first embodiment of the invention, the first element is a central core surrounded by a layer of the said material.

According to a first alternative form of this first embodiment, the second element is an electrical wire wound around the layer of the said material.

According to a second alternative form of this first embodiment, the second element is a perforated metal layer surrounding the layer of the said polymer material.

According to a second embodiment, the first and second elements are two parallel electrical wires.

The polymer-based material, or polymer material, of the invention may comprise one or more organic polymers. The choice of the polymer or polymers is preferably limited to polymers that can be worked easily by extrusion, i.e. extrudable polymer, notably where the extrusion temperature is below the temperature at which any filler or fillers that might be contained within the polymer material decompose or degrade.

Thus, in a preferred embodiment, the polymer material is extruded.

Furthermore, the choice of polymer or polymers from which the polymer material is made may be limited by the mechanical properties of the polymer material that are ultimately desired, notably in terms of the elongation at break of the polymer material, so as to avoid cracks forming, for example when the detection cable is wound around a drum for transport.

For preference, the polymer material is made up mainly of an organic polymer or of a mixture of organic polymers.

The polymer material of the invention may be of two types.

The first type is such that the polymer material may comprise a non-soluble first polymer preferably one that is non-soluble in water, associated with a desiccant filler (i.e. with a filler that is moisture sensitive). In this case, the first polymer may more particularly be chosen from:
  olefin polymers such as notably vinyl acetate polymers for example ethylene vinyl acetate (EVA) copolymers or ethylene polymers such as polyethylene octene (PEO) copolymers for example, and
  polycaprolactones,
  or a mixture thereof.

In one particular embodiment, the first type of polymer material may contain only one polymer matrix and one or more desiccant fillers, the polymer matrix including at least said first polymer, the latter notably being predominant in said matrix.

The term "polymer" is used in the description in its broadest possible sense and may cover both copolymers and homopolymers.

What is meant by a "desiccant filler" is a filler that can dry out, notably under the effect of an increase in temperature. The desiccant filler of the invention therefore includes hygroscopic fillers which also have this property. The desiccant filler of the invention is therefore also capable of retaining moisture (i.e. of absorbing moisture).

The desiccant filler of the invention therefore has reversible properties of releasing water and of retaining water, depending on the surrounding temperature of the device.

The desiccant filler may be an organic or inorganic filler or a mixture of the two.

By way of example, it may be chosen from anhydrous calcium sulfate, cellulose, starch, and polyvinyl alcohol, or a mixture thereof.

The amount of desiccant filler in the polymer material of the invention can vary according to the type of filler used.

The minimum amount is conventionally defined so as to have a significant variation in electrical resistance to show a relative humidity level that is higher than the level of relative humidity present in the usual environment in which said cable is to be used.

The maximum amount is typically defined so that it does not have a detrimental impact on the mechanical properties of the polymer material, notably in terms of its elongation at break, so as to avoid cracks forming in the polymer material notably when the detection cable is wound around a drum for transport.

By way of example, the amount of desiccant filler may be at least 5 parts by weight per 100 parts by weight of polymer(s) in the polymer material, preferably at least 10 parts by weight per 100 parts by weight of polymer(s) in the polymer material, and preferably at least 30 parts by weight per 100 parts by weight of polymer(s) in the polymer material. It may also be comprised between 100 and 200 parts by weight per 100 parts by weight of polymer(s) in the polymer material.

The second type is such that the polymer material may comprise a non-soluble second polymer, preferably one that is non-soluble in water, and that is sensitive to moisture: a moisture sensitive filler is then no longer necessary in this type of polymer material. In this case, the second polymer can be chosen from the polymers that can be obtained from starch. By way of example, mention may be made of the product known as Materbi and marketed by the company Novamont, which is a blend of starch-based polymers also containing polycaprolactone. The starch cannot then be considered to be a filler, but actually corresponds to the polymer matrix of the polymer material.

In one particular embodiment, the second type of polymer material may contain only one polymer matrix, the polymer matrix including at least said second polymer, the latter notably being predominant in said matrix.

Of course, a mixture of the first type and of the second type of polymer material may be imagined. Likewise, both the first and the second type of polymer material may contain other polymers and/or other fillers.

For example, the polymer material of the invention may further comprise at least an electrically conducting filler and/or at least an electrically conducting polymer, thus allowing the initial electrical resistance of said polymer material to be reduced.

In the present invention, it will be preferable to use the first type of polymer material (cf. the first non-soluble polymer associated with the desiccant filler). This first type (as opposed to the second type of polymer material) advantageously allows the mechanical, rheological and water uptake properties of the polymer material to be adjusted precisely and easily, notably by altering the amount of desiccant filler incorporated into the first polymer.

The apparatus for measuring the electrical resistance between the two electrically conducting elements may be a megohmmeter.

In one particular embodiment, the device of the invention may further comprise a heating means. This heating means is intended to allow the water captured within the polymer material to evaporate, thus allowing the cable to revert back to its initial state before a new moisture adsorption cycle.

This heating means may for example be a heating cable positioned close to and along the detection cable.

In the present invention, the polymer-based material may or may not be crosslinked.

According to a first alternative form, she polymer-based material is not crosslinked. Thus, the method of manufacturing said material remains simple and easy to implement.

According to a second alternative form, the polymer-based material is crosslinked using techniques well known to those skilled in the art. Thus, even though the method of manufacturing a crosslinked polymer material requires the use of techniques in addition to those used simply to obtain a non-crosslinked polymer material, the crosslinked polymer material has the advantage that it can be used at far higher temperatures than can an non-crosslinked polymer material, particularly when the device of the invention includes said heating means. At higher heating temperatures, the evaporation of the water captured within the crosslinked polymer material will therefore be more rapid. Typically, the bonds created during the crosslinking allow the crosslinked polymer material to be far less temperature sensitive.

BRIEF DESCRIPTION OF THE DRAWINGS

Further features and advantages of the present invention will become apparent from reading the examples that will follow, with reference to the annotated figures, said examples and figures being given by way of nonlimiting illustration.

FIG. 1 is a perspective view of a first alternative form of a first embodiment of a detection cable according to the invention.

FIG. 2 is a perspective view of a second alternative form of a first embodiment of a detection cable according to the invention.

FIG. 3 is a perspective view of a second embodiment of a detection cable according to the invention.

FIG. 4 is a perspective view of the detection cable of FIG. 3, further comprising a heating cable.

DETAILED DESCRIPTION

Figure 5:
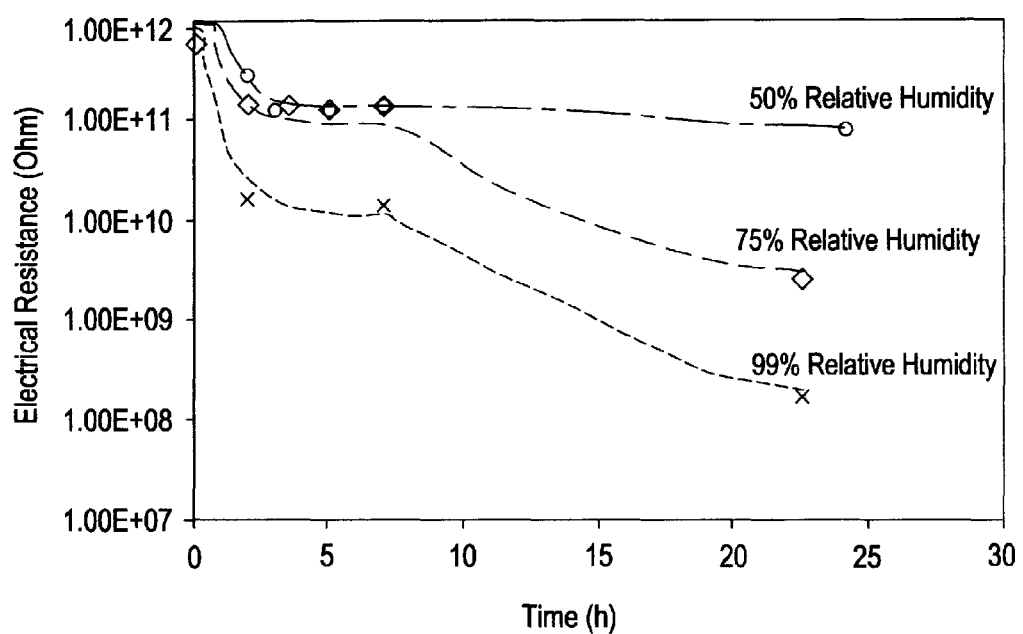
FIG. 5 depicts the change, as a function of time, in the electrical resistance of a detection cable comprising a first example of polymer material according to the invention, for different relative humidity levels.

For clarity, the same elements have been denoted by identical references. Likewise, only those elements that are essential for understanding the invention have been depicted, and then schematically and not to scale.

FIG. 1 is a perspective view of a first alternative form of a first embodiment of a detection cable 10a according to the invention.

This cable comprises a central first electrical wire 1 surrounded by an extruded layer 3 of a polymer material according to the invention, of a thickness that is substantially constant along the length of the cable. A second electrical wire 2a helically surrounds the layer 3. The turns of the helix of the second electrical wire are evenly spaced along the length of the cable.

FIG. 2 is a perspective view of a second alternative form of a first embodiment of a detection cable 10b according to the invention.

This cable comprises a central first electrical wire 1 surrounded by an extruded layer 3 of a polymer material according to the invention, of a thickness that is substantially constant along the length of the cable. A metal layer of the tube type surrounds the layer 3, this layer being perforated with openings 4 positioned uniformly along the length of the cable.

For preference, the detection cables of the present invention, such as those depicted in FIGS. 1 to 4 for example, have no outer protective sheath surrounding the first and second electrically conducting elongate elements and the polymer material.

More specifically, the detection cable of the invention comprises only the first and second electrically conducting elongate elements and the polymer material.

If the detection cable of the invention were to comprise said protective sheath, it would be essential for its physico-chemical properties and/or its structure to allow water to come into contact with the polymer material. For example, this protective sheath could have holes and/or be made of a water-sensitive material.

FIG. 3 is a perspective view of a second embodiment of a detection cable 10c according to the invention.

This cable comprises a first electrical wire 1 and a second electrical wire 2c which are substantially parallel along the length of the cable. These two wires 1 and 2c are, on the one hand, separated along the length of the cable by a substantially constant thickness of an extruded polymer material 3 according to the invention and, on the other hand, covered with a layer of said polymer material 3. The polymer material 3 separating the two wires and covering them is obtained by extrusion.

FIG. 4 is a perspective view of the detection cable 10c of FIG. 3, further including a heating cable 5.

The heating cable 5 is surrounded by the polymer material 3 and comprises two insulated electrically conducting wires 5a, 5b and an uninsulated electrically conducting wire 5c, these three wires being surrounded by a metal jacket 5d. The uninsulated electrically conducting wire 5c is connected to the electrical ground and is in contact with the metal jacket 5d.

The heating cable advantageously allows optimal removal of the residual moisture contained in the polymer material thus returning the detection cable rapidly to its initial state containing little or no residual water (i.e. prior to the detection of moisture).

Of course, this embodiment is not in any way limiting and it is quite conceivable for example to have said heating cable on the outside of the detection cable.

EXAMPLES

A detection cable as depicted in FIG. 3 is produced using two copper wires of 1.5 mm$^2$ cross section laid parallel to one another in a first example of non-soluble and moisture-sensitive polymer material, the distance between the two copper wires being kept constant at 1 mm. The thickness of the layer of polymer material covering the two wires is also 1 mm. Said polymer material, which is extruded around these two copper wires, is made up of:

an ethylene vinyl acetate copolymer containing 28% of vinyl acetate groups, marketed by Exxon Mobil under the reference Escorène UL 0328, and approximately 150 parts by weight of an inorganic desiccant filler as anhydrous calcium sulfate marketed by WA Hammond Drierite LTD under the reference Drierite.

The detection cable thus obtained is 5 meters long. The two copper wires of one of the ends of the detection cable are connected to a megohmmeter to measure the electrical resistance between the two copper wires. The detection cable and the megohmmeter together form an electrical detection device according to the invention.

The detection cable is introduced into an environmental test chamber with a controlled relative humidity level, and the electrical resistance between the two copper wires is measured over time for 24 hours. The temperature is kept constant at 25° C.

FIG. 5 depicts the change, as a function of time, in the electrical resistance of the detection cable as described hereinabove and depicted in FIG. 3, for different relative humidity levels. The relative humidity is the ratio between the pressure of water vapor present in the air considered (the partial pressure of the water in the air) and the theoretical saturation pressure. It is expressed as a percentage.

In FIG. 5, the initial electrical resistance of the detection cable is of the order of $1 \times 10^{12}$ ohm. This value corresponds to the reference of the measurements with a relative humidity level of the order of 40%.

For a relative humidity level of 99%, the resistance drops from a teraohm to around one hundred megohms, which means to say that the electrical resistance drops by 4 decades. For a relative humidity level of 75%, the drop in electrical resistance is of the order of 3 decades, and for a relative humidity level of 50%, the drop is just 1 decade.

For preference, the critical relative humidity levels that it is desirable to detect are those between 80 and 100%.

Reversibility tests were also carried out. These tests involve placing the detection cable at 25° C. with a humidity level of 99% for 24 h (i.e. cycle 1). Electrical resistance measurements were taken at 0, 2, 5, 7 and 24 h.

Once the 24-hour cycle 1 was completed, the cable was dried for 24 h at 60° C. in an oven with a relative humidity level of 40%. A further cycle (i.e. cycle 2) identical to cycle 1 was then performed.

The results are collated in table 1 below.

TABLE 1

| | Cycle 1 | | Cycle 2 |
|---|---|---|---|
| Time (h) | Electrical resistance (ohm) | Time (h) | Electrical resistance (ohm) |
| 0 | 9.00E+11 | 0 | 2.52E+12 |
| 2 | 1.60E+10 | 2 | 1.70E+10 |
| 5 | 1.17E+10 | 5 | 1.25E+10 |
| 7 | 1.35E+10 | 7 | 1.30E+10 |
| 24 | 1.63E+08 | 24 | 1.01E+08 |

Other reversibility tests involve placing the detection cable at 25° C., with a humidity level of 75% for 24 h (i.e. cycle 1). Electrical resistance measurements were taken at 0, 2, 5, 7 and 24 h.

Once the 24-hour cycle 1 was completed, the cable was dried for 24 h at 60° C. in an oven with a relative humidity level of 40%. A further cycle (i.e. cycle 2) identical to cycle 1 was then performed.

The results are collated in table 2 below.

TABLE 2

| | Cycle 1 | | Cycle 2 |
|---|---|---|---|
| Time (h) | Electrical resistance (ohm) | Time (h) | Electrical resistance (ohm) |
| 0 | 5.62E+11 | 0 | 5.62E+11 |
| 2 | 1.38E+11 | 2 | 1.65E+11 |
| 5 | 1.27E+11 | 5 | 1.16E+11 |
| 7 | 1.30E+11 | 7 | 1.03E+11 |
| 24 | 2.50E+09 | 24 | 2.50E+09 |

Other reversibility tests involve placing the detection cable at 25° C., with a humidity level of 40% for 24 h (i.e. cycle 1). Electrical resistance measurements were taken at 0, 2, 5, 7 and 24 h.

Once the 24-hour cycle 1 was completed, the cable was dried for 24 h at 60° C. in an oven with a relative humidity level of 40%. A further cycle (i.e. cycle 2) identical to cycle 1 was then performed.

The results are collated in table 3 below.

TABLE 3

| | Cycle 1 | | Cycle 2 |
|---|---|---|---|
| Time (h) | Electrical resistance (ohm) | Time (h) | Electrical resistance (ohm) |
| 0 | 1.00E+12 | 0 | 1.84E+12 |
| 2 | 1.52E+11 | 2 | 2.81E+11 |
| 5 | 1.25E+11 | 5 | 1.21E+11 |
| 7 | 1.07E+11 | 7 | 1.27E+11 |
| 24 | 8.90E+10 | 24 | 8.30E+10 |

The results of tables 1 to 3 demonstrate that the detection cable of the invention can be re-used once dry, because the initial electrical resistance (at 0 h) on the one hand, and after 24 h on the other, in a damp environment (99%, 75% or 40% relative humidity) remains substantially unchanged between cycle 1 and cycle 2.

A detection cable as depicted in FIG. 3 is produced using two copper wires of 1.5 mm$^2$ cross section laid parallel to one another in a second example of non-soluble and moisture-sensitive polymer material, the distance between the two copper wires being kept constant at 0.24 mm. The thickness of the layer of polymer material covering the two wires is 1 mm. Said polymer material extruded around these two copper wires is made up of:
- 70 wt % of a polycaprolactone marketed by Perstorp, under the reference CAPA 6800, and
- 30 wt % of an organic desiccant filler such as polyvinyl alcohol marketed by Kruaray, under the reference Kuraray CP1220T10.

The detection cable thus obtained is 5 meters long. The two copper wires of one of the ends of the detection cable are connected to a megohmmeter to measure the electrical resistance between the two copper wires. The detection cable and the megohmmeter together form an electrical detection device according to the invention.

The detection cable is introduced into an environmental test chamber with a controlled relative humidity level, and the electrical resistance between the two copper wires is measured over time for 48 hours. The temperature is kept constant at 25° C.

Figure 6:
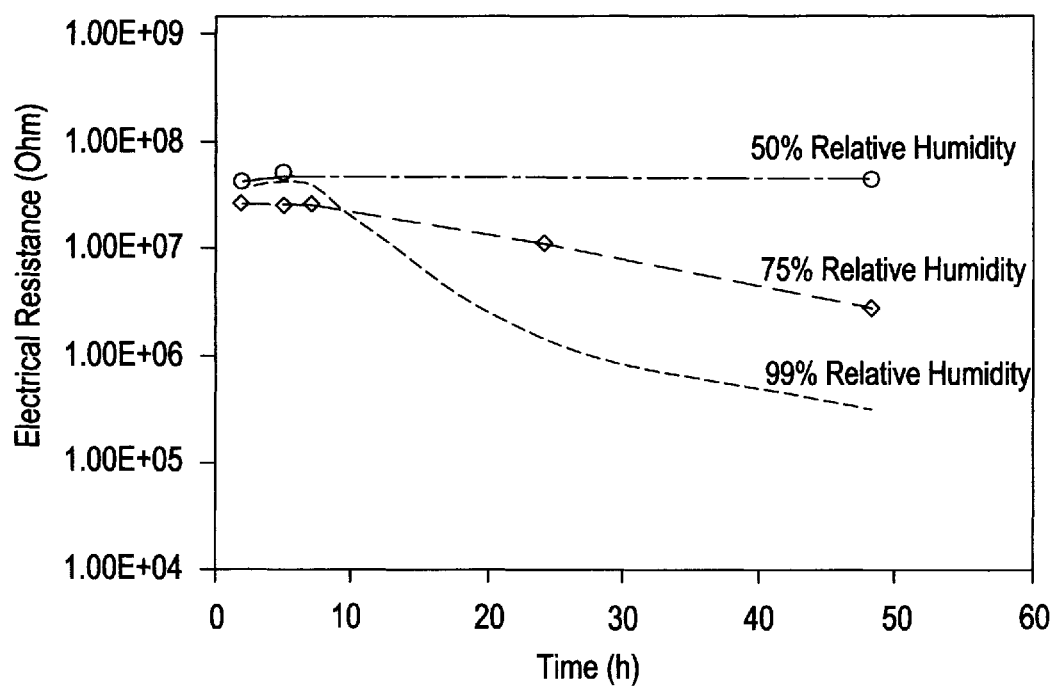
FIG. 6 depicts the change, as a function of time, in the electrical resistance of a detection cable comprising a second example of polymer material according to the invention, for different relative humidity levels.

FIG. 6 depicts the change, as a function of time, in the electrical resistance of the detection cable as described hereinabove and depicted in FIG. 3, for different relative humidity levels. The relative humidity is the ratio between the pressure of water vapor present in the air considered (the partial pressure of the water in the air) and the theoretical saturation pressure. It is expressed as a percentage.

In FIG. 6, the initial electrical resistance of the detection cable is of the order of 20 MOhm (megohms). This value corresponds to the reference of the measurements with a relative humidity level of the order of 40%.

For a relative humidity level of 99%, the resistance drops from 20 Mohm to 200 kOhm (kiloohm), which means to say that the electrical resistance drops by 2 decades. For a relative humidity level of 75%, the drop in electrical resistance is of the order of 1 decade, and for a relative humidity level of 50%, the drop is less than 1 decade.

For preference, the critical relative humidity levels that it is desirable to detect are those between 80 and 100%.

The invention claimed is:
1. Electrical device for detecting moisture, comprising:
   a detection cable made up of a first element and of a second element, which elements are elongate and electrically conducting and separated by a single polymer-based material; and an electrical resistance measurement appliance intended to measure the electrical resistance between the first and second elements of the said cable, wherein the polymer based material is a non-soluble and moisture-sensitive material selected from a group consisting of a first polymer non-soluble in water, associated with a desiccant filler, a second polymer non-soluble in water and moisture sensitive, and a mixture thereof.

2. Device according to claim 1, wherein the first element is a central core surrounded by a layer of the said material.

3. Device according to claim 2, wherein the second element is an electrical wire wound around the layer of the said material.

4. Device according to claim 2, wherein the second element is a perforated metal layer surrounding the layer of the said material.

5. Device according to claim 1, wherein the first and second elements are two parallel electrical wires.

6. Device according to claim 1, wherein the material is extruded.

7. Device according to claim 1, wherein the first polymer is selected from the group consisting of olefin polymers and polycaprolactones, and a mixture thereof.

8. Device according to claim 1, wherein the desiccant filler is selected from the group consisting of anhydrous calcium sulfate, cellulose, starch, and polyvinyl alcohol, and a mixture thereof.

9. Device according to claim 1, wherein the second polymer is selected from the group consisting of the polymers that can be obtained from starch.

10. Device according to claim 1, wherein the material further comprises at least an electrically conducting filler and/or an electrically conducting polymer.

11. Device according to claim 1, wherein said device further comprises a heating means.

12. Electrical device for detecting moisture, comprising:

a detection cable made up of a first element and of a second element, which elements are elongate and electrically conducting and separated by a polymer-based material; and an electrical resistance measurement appliance intended to measure the electrical resistance between the first and second elements of the said cable, wherein the polymer based material is a non-soluble and moisture-sensitive material selected from a group consisting of a first polymer non-soluble in water, associated with a desiccant filler, a second polymer non-soluble in water and moisture sensitive, and a mixture thereof, wherein the moisture-sensitive material is a material that has physiochemical properties that are necessary and sufficient for moisture to be adsorbed onto its surface and diffused through said material.

* * * * *